United States Patent [19]

Kwiatkowski

[11] Patent Number: 4,936,776
[45] Date of Patent: Jun. 26, 1990

[54] DENTAL PRODUCT AND METHOD UTILIZING TRANSLUCENT MATERIAL

[76] Inventor: Stephen J. Kwiatkowski, 1355 Crestwood Dr., Morgantown, W. Va. 26505

[21] Appl. No.: 215,220

[22] Filed: Jul. 5, 1988

[51] Int. Cl.$^5$ .............................................. A61C 5/08
[52] U.S. Cl. .................................... 433/220; 433/223; 433/221
[58] Field of Search .................... 433/220, 221, 222.1, 433/223, 224, 225, 201.1, 202.1, 203.1, 204, 175; 264/16, 19, 20

[56] References Cited

U.S. PATENT DOCUMENTS

| | | | |
|---|---|---|---|
| 3,732,087 | 5/1973 | Grossman | 65/33 |
| 3,839,055 | 10/1974 | Grossman | 106/39.6 |
| 4,230,455 | 10/1980 | Hidaka et al. | 433/202.1 |
| 4,431,420 | 2/1984 | Adair | 433/199 |
| 4,713,006 | 12/1987 | Hakamatsuka et al. | 433/175 |

OTHER PUBLICATIONS

Pastrana, Miguel A., D.M.D., "Restoration of Endodontically Treated Teeth", in Thayer, Keith E., ed., Fixed Prosthodontics, Year Bk. Med. 600, Jan. 1984.
Shillingberg, Herbert, et al., "Restoration of Endodontically Treated Teeth", in Shillingbert, Herbert, et al., Fundamentals of Fixed Prosthodontics, Quint Pub. Co. 339, 1978.
Geller et al., "The Willi's Glas Crown: A New Solution in the Dark and Shadowed Zones of Esthetic Porcelain Restorations", Quintessence of Dental Technology, Jul./Aug. 1987, pp. 233-242.

*Primary Examiner*—John J. Wilson
*Attorney, Agent, or Firm*—Webb, Burden, Ziesenheim & Webb

[57] ABSTRACT

A dental product and method utilizing a translucent construct as the post or post-and-core of a dental restoration. In normal tooth structure, the prismatic and refractive enamel carries light into the dentin and root, transilluminating the gingiva and contributing to its pink color. The use of a translucent post or post-and-core structures preserves this normal transillumination and minimizes or eliminates gingival discoloration adjacent a dental restoration.

20 Claims, 1 Drawing Sheet

DENTAL PRODUCT AND METHOD UTILIZING TRANSLUCENT MATERIAL

FIELD OF THE INVENTION

This invention relates to the restoration of endodontically treated teeth, particularly without causing discoloration of the gingiva.

BACKGROUND OF THE INVENTION

Endodontic treatment often saves a tooth from imminent extraction, but does not alone restore the tooth to its role as a long-term functioning member of the mouth. For example, endodontically treated teeth are more prone to fracture than vital teeth, perhaps because loss of nerve and vascular supply leads to loss of internal moisture and commensurate reduction in resilience of tooth structure. Furthermore, if caries has caused the death of the pulp of the tooth, eventuating the need for endodontic treatment, carious lesions in the tooth structure may cause the tooth to split under masticatory loads.

Certain well-known products and methods are available for use in the restoration of endodontically treated teeth. Cementing a metal post within the canal of an endodontically treated tooth is a common clinical procedure. If some or all of the coronal structure of the tooth has been compromised or lost, the post is fitted with a core to replace lost tooth structure. The combined post and core, sometimes referred to as a dowel and core or a dowel-core, is often fabricated of stainless steel or titanium or gold alloys. Typically, the restoration is completed with a crown.

Clinical considerations and methods with respect to metal posts and cores, and exemplary prefabricated posts, are generally discussed in Pastrana, Miguel A., D.M.D., "Restoration of Endodontically Treated Teeth", in Thayer, Keith E., ed., *Fixed Prosthodontics*, Year Bk. Med., 600 p., January, 1984. Pastrana discloses, for example, that endodontic treatment should be carefully preplanned so that the material from the filled tooth canal can be easily and adequately eliminated, the material of choice being gutta-percha. At the time of restoration, the entire diameter of gutta-percha is removed from the canal either to at least two-thirds of the root's length or to a depth equal to the length of the tooth's normal clinical crown. A pattern for the post and core is then made of wax or polymer resin, formed and built in the mouth, with the completed pattern then being sprued, invested and cast. Alternatively, prefabricated systems are available in which a prefabricated core is cemented in place with subsequent building up of the core with amalgam or composite resin.

Another publication in which metal post/core structures and the use thereof are discussed include Shillingberg, Herbert, et al., "Restoration of Endodontically Treated Teeth", in Shillingberg, Herbert, et al., *Fundamentals of Fixed Prosthodontics*, Quint Pub. Co., 339 p., 1978. Metal structures are discussed throughout.

Despite its many advantages, the post-and-core, or dowel-core, of an anterior restoration routinely presents subtle yet invidious cosmetic aberrations. Even with the most natural-looking crown atop the restoration, the restored tooth inevitably has an unmistakable "false" look attributable to its adjacent grayish or darkened gingiva. For example, as Geller et al. disclose in "The Willi's Glas Crown A New Solution in the Dark and Shadowed Zones of Esthetic Porcelain Restorations", *Quintessence of Dental Technology*, July/August 1987, pp. 233–242, the most challenging need for reversal of gingival discoloration occurs when a porcelain-fused-to-metal crown is mounted within a dark nonvital tooth having a metal post foundation. Geller et al. explain, at page 239, that the combination of the dark root, opaque crown coping, metal post foundation, and root canal filling material frequently results in the entire tissue area, including attached gingiva and mucosa, acquiring a blue-gray color. Notwithstanding the stated assumption that the metal "post foundation must remain" within the restored tooth, Geller et al. suggest certain crown structures which partially reduce gingival discoloration. A need therefore persists for a product and method for the improved reduction or elimination of gingival discoloration adjacent to dowel-core restored teeth.

SUMMARY OF THE INVENTION

In order to meet this need, the present invention is a dental product and method utilizing translucent material as the post or post-and-core of a dental restoration. In normal tooth structure, the prismatic and refractive enamel carries light into the dentin and root, transilluminating the gingiva and contributing to its pink color. The use of translucent post or post-and-core structures preserves this normal transillumination and minimizes or eliminates gingival discoloration adjacent a dental restoration.

DETAILED DESCRIPTION OF THE INVENTION

Figure 1:
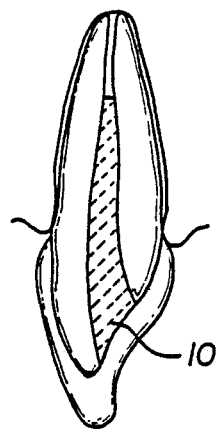
FIG. 1 is a sectional view of an anterior tooth, restored in accordance with the present invention, in which no coronal tooth structure has been lost.

In view of the nature of the present invention as identified above, the fabrication of tooth restoration foundation posts, dowels and/or cores having translucent characteristics, selection of the appropriate materials forms a critical part of the present invention. Materials suitable for preparing translucent posts and/or cores must have not only the required light refractive characteristics but must also exhibit strength and resilience properties which enable the resultant structures to withstand the various chemical, structural and masticatory forces of the mouth.

It should be noted at the outset that, in the context of the present invention, the term "translucent" has been given a specialized meaning: a material is translucent as long as it is not opaque. Accordingly, the translucent materials of the present invention should be understood to include transparent materials, i.e., those materials which permit completely unobstructed passage of light, as well as materials which permit some degree of passage of light. It is also understood that structures disclosed and claimed herewith as translucent preferentially include translucent adjuncts, including translucent layers of bonding agents or resins.

One of the two preferred translucent materials for the preparation of translucent posts and/or cores is the castable phosphate-bound apatite-containing composition available as CERAPEARL TM by Kyocera. Other castable phosphate-bound, apatite-containing dental construct compositions and their equivalents may be substituted. CERAPEARL TM has translucency and radiopacity closely matching tooth enamel, and apatite crystals formed during crystallization of CERAPEARL TM structures make the structures strong and wear-resistant. Kyocera, however, suggests CERAPEARL TM for use in only crowns, inlays, onlays and laminate veneers, not for posts or cores.

The second translucent material preferred for use in the present invention is the DICOR TM castable glass-ceramic compositions known in the art. Various other castable glass-ceramics, also known in the dental restoration arts, are also suitable for use. Representative of other castable glass-ceramics are three patented compositions, disclosed in U.S. Pat. No. 3,732,087, U.S. Pat. No. 3,839,055 and U.S. Pat. No. 4,431,420, each incorporated herein by reference. The latter patent discloses a glass-ceramic having tetrasilicic fluormica in its predominant crystal phase, and the first two patents listed pertain to tetrasilicic mica glass-ceramics. As disclosed in U.S. Pat. No. 4,431,420, mica-containing glass-ceramics demonstrate a relatively unique property which renders them particularly desirable in applications such as dental constructs. The materials manifest deviations from brittle behavior which permit them to withstand point impact with limited fracture propagation. This capability of mica-containing glass ceramics is due to the ability of the crystal phase to flow plastically to some extent, through translational gliding along the basal or cleavage plane.

Unless prefabricated posts are employed, the preparation and bonding of the translucent post and/or core is customized for each patient. No special consideration in the preliminary endodontic treatment is necessary except that gutta-percha is recommended (as discussed above) and eugenol-containing materials should not be used; the presence of eugenol in the final fill interferes with bonding procedures later. The classic dowel preparation is basically employed, in the practice of the present invention, in that the appropriate depth of gutta-percha filling material is removed. (Current revisions being considered in dowel preparation and in restoring endodontically treated teeth emphasize a conservative approach, i.e., maintaining as much tooth structure as possible. The present invention is compatible with this new direction.) The tooth preparation is cut as ideally as possible for a porcelain jacket crown, with jagged edges and angles being smoothed. The axial walls of the crown preparation are blended to the post or dowel preparation on a curve to prevent the formation of an internal fracture plane. An impression of the tooth preparation is taken by means known in the art, such as for example by using a spiral lentulo filler to load the tooth. Typically, an adhesive-coated paper clip is inserted to supply rigidity and support. Two impressions are ordinarily made to confirm accuracy and to assure stress free insertion in the mouth.

At this point, the posts or dowel-cores are prepared from the selected materials. The materials themselves (starting or intermediate materials or constituents thereof) need not be translucent as long as the final prepared post, post and core or dowel-core is translucent. When ceramic or glass-ceramic materials are used, the post preparation protocol described below is typical. Other compositions may be used by techniques appropriately adopted to suit them.

The impressions are sent to the laboratory, poured in die stone and lubricated in preparation of making a wax pattern. An opposing counter model to check the occlusal relationship of the wax pattern and to assure an ideal crown preparation form is required. The wax pattern is formed around a plastic endowel and corrected with soft wax to the dowel portion of both stone models. The coronal portion of the crown preparation may thereafter be completed as is known in the art.

The wax pattern is subsequently invested in the castable ceramic investment material according to manufacturer's directions. The invested pattern is burned out, cast, recovered and ceramed in a routine manner. The fit and finish of the ceramed post is confirmed on both models. The finished post is etched to provide an optimum bonding surface, and the post is returned to the clinician for insertion.

The temporized tooth is cleaned and prepared for the casting try-in. The ceramic post should seat completely and passively. Because the walls of the dowel preparation are all dentin, a dentin bonding agent is used to establish a strong bonding potential with the resin cement used to cement the post. Two materials which are currently available that provide bonding strengths approaching that of resin to etched enamel are Tenure by Den Mat and G.L.U.M.A. by Columbia Dental Supply. The etched ceramic dowel is treated with a silane bonding agent, and a light/chemical cured resin cement (known in the art) is mixed and applied to the ceramic post. The post is carried to the mouth and seated, the excess cement is removed and a curing light is applied from the labial and lingual surfaces for 60 seconds each side. The light may not penetrate to the entire depth of the prepared canal but the chemical curing phase of the cement assures complete polymerization in about eight minutes. The post restored tooth subsequently may be treated as a routine crown preparation.

As a result of the above technique, exemplified in greater detail in the Examples, below, transilluminated teeth appear identical to their vital neighbors. Furthermore, because the restoration is chemically bonded to the root structure, the restoration provides for structural reinforcement of the tooth. In addition, when glass-ceramic or other ceramic materials are used, the fact that they are not excessively strong provides a "safety valve" when the tooth is subjected to excessive traumatic forces. Although at least a number of glass-ceramic or ceramic materials are strong enough to withstand normal and functional oral stresses, when these forces are exceeded—as in the case of a blow to the mouth—the relatively brittle nature of the ceramic material allows fracture to occur at the external fracture plane established by the gingival shoulder of the tooth preparation. This allows the opportunity to salvage the tooth and restore the root again. Cemented metal posts, on the contrary, do not break under excessive force but instead transfer the excessive force into the root, causing fractured roots which must be extracted and necessitating construction of a bridge.

Figure 5:
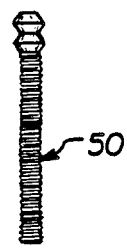
FIGS. 5–9 illustrate side elevational views of various prefabricated posts.
Figure 6:
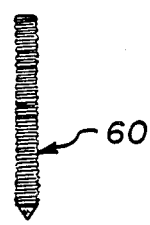
Figure 7:
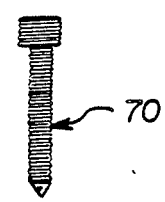
Figure 8:
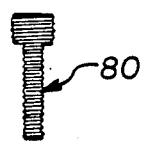
Figure 9:
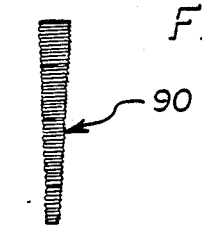

In the event the use of a prefabricated post is preferred, the post designs shown in FIGS. 5-9 may be used, along with a wide variety of other designs. FIG. 5 illustrates a prefabricated post 50 in side elevational view, having a shaft and an angle-bodied head. The surfaces of the shaft of the prefabricated post 50 are lightly etched in spaced serrations, to provide the rough surface which maximizes dentinal bonding. FIG. 6 illustrates a prefabricated post 60 which includes a cylindrical shaft having an angled tip, lightly edged in a serrated pattern as is the prefabricated post 50 of FIG. 5. The prefabricated post 70 of FIG. 7 is similar to the prefabricated post 60 of FIG. 6, except that the shaft terminates in a head having a diameter larger than the diameter of the shaft. The prefabricated post 80 of FIG. 8 is similar to the prefabricated post 70 of FIG. 7, except that the angled tip is not included and the shaft instead has a blunt cylindrical tip. The prefabricated post 90 of FIG. 9 is a tapered or conical post having a maximum diameter at the upper end and a minimum diameter at the lower end.

The prefabricated posts 50, 60, 70, 80 and 90 are all constructed of translucent material according to the present invention. The prefabricated posts may be prepared according to means known in the art, and customarily will be made commercially available in a wide range of sizes, usually in kits or packages from which the clinician can select the appropriate size for a given patient and a given tooth. The posts are bonded with a dentin bonding agent by the same techniques as are used with cast posts (discussed above and in the accompanying Examples) and the cores are built up with translucent composite or, if necessary, amalgam or other core build-up materials, by means known in the art. Obviously, building up of cores with translucent composites known in the art is preferred in the practice of the present invention.

Although the translucent custom-cast and prefabricated posts of the invention have been described generally above, the following Examples are illustrative of specific materials, methods and structures according to the present invention. The following Examples are not, however, limiting as to the invention, in which wide latitude of variation is contemplated.

EXAMPLE I

FIG. 1 is a sectional view of an anterior tooth subsequent to restoration with a translucent post 10. The tooth anatomy of FIG. 1 is that known in the art, and the translucent post 10 is shown affixed within the dentin and underneath the cap of the tooth. FIG. 1 represents a tooth in which no loss of coronal tooth structure occurred prior to restoration.

Initial endodontic treatment of the tooth of FIG. 1 proceeded to an ultimate gutta-percha filling of the root canal. At the time of restoration, the gutta-percha was removed with a reamer to a depth of two-thirds of the root's length. The tooth preparation was cut, in the manner known in the art, in the configuration ideal for a porcelain jacket crown, with jagged edges and angles being smoothed. The axial walls of the crown preparation were blended to the post preparation on a curve to prevent the formation of an internal fracture plane. Two impressions of the completed tooth preparation were taken and sent to the laboratory.

At the laboratory, the impressions were used to make a wax pattern. The pattern was used to prepare a cast translucent post from DICOR TM glass-ceramic material. Preparation of the DICOR TM post was accomplished by means known in the art as documented in the product literature published by the manufacturer. The finished post was etched to provide an optimum bonding surface, and the post was returned to the clinician for insertion in the prepared tooth.

The cast post 10 was confirmed to fit properly in the tooth of FIG. 1, and the dentin of the tooth was prepared with the dentin bonding agent "TENURE". To use the TENURE, the tooth was isolated from any possibility of moisture, and the TENURE components were applied according to the manufacturer's directions. The etched ceramic dowel was treated with a silane bonding agent known in the art and Dual Cement, from Vivadent (a light/chemical cured resin cement) was mixed and applied to the post 10. The post 10 was carried to the mouth and seated, the excess cement was wiped away and a curing light was applied to the bonding agents from the labial and lingual surfaces for 60 seconds each side. The cured Dual Cement was translucent. The post 10 and restored tooth of FIG. 1 were then ready for treatment as a routine crown preparation.

EXAMPLE II

Figure 2:
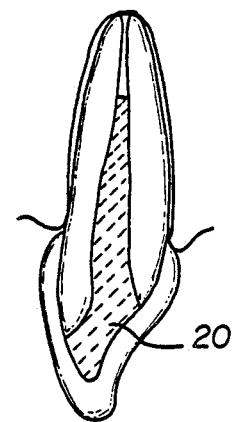
FIG. 2 is a sectional view of an anterior tooth, restored in accordance with the present invention, in which a portion of the coronal tooth structure has been replaced.

Referring now to FIG. 2, the process disclosed in Example I were followed with the exception that G.L.U.M.A. dentin bonding agent from Columbia Dental Supply was substituted for the TENURE composition in the preparatory treatment of the dentinal surfaces. The only other difference in the practice of the invention, to eventuate the restored tooth of FIG. 2, was the fashioning of a post-and-core structure by impression in view of the partial absence of coronal tooth structure. Axial walls of the crown preparation were blended to the post preparation on a curve, to prevent the formation of an internal fracture plane. Impression, pattern preparation, casting of the post 20 and insertion in the prepared tooth were accomplished in accordance with Example I.

EXAMPLE III

Figure 3:
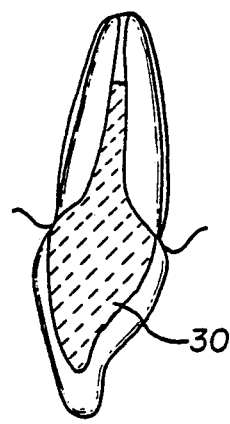
FIG. 3 is a sectional view of an anterior tooth, restored in accordance with the present invention, in which all of the coronal tooth structure has been replaced.

The process according to Example II were followed in the casting and insertion of post and core 30, with FIG. 3 illustrating a restored tooth in which all of the coronal tooth structure was removed prior to tooth restoration.

EXAMPLE. IV

Figure 4:
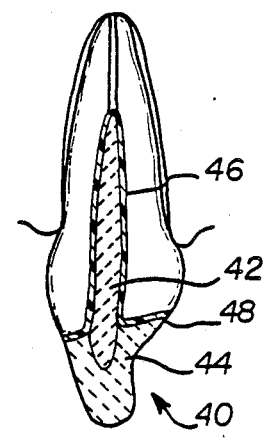
FIG. 4 is a sectional view of a restored anterior tooth having a crown fired to the post.

Referring now to FIG. 4, a variation of the present invention includes the restored tooth 40 having a porcelain crown 44 fired to the post 42. The post 42 was prepared according to Example I, but prior to insertion in the prepared tooth, the porcelain crown 44 was fired to the translucent post 42. The post 42 was bonded to the dentin by means of a dentinal bonding agent layer 46, which layer represents not only the applied dentin bonding agent (G.L.U.M.A.) per se but also the resin bonding agent (Dual Cement), and the remainder of the combined post 42 and porcelain crown 44 was bonded to the tooth preparation by means of a known porcelain bonding agent layer 48 as illustrated.

Although the invention has been described specifically in its various embodiments, above, the invention is to be limited only insofar as is set forth in the accompanying claims.

I claim:

1. A tooth restoration having a post and a crown, the improvement comprising said post being translucent and further being attached to said crown.

2. In a tooth restoration according to claim 1, the improvement further comprising said translucent post having a translucent core adjacent thereto.

3. In the tooth restoration according to claim 2, the improvement further comprising said translucent post and said translucent core consisting of a translucent ceramic material.

4. In the tooth restoration according to claim 3, the improvement further comprising said ceramic material being selected from the group consisting of glass-ceramics containing tetrasilicic mica and glass-ceramics containing tetrasilic fluormica.

5. In the tooth restoration according to claim 2, the improvement further comprising said translucent post and said translucent core consisting of an apatite-containing dental construct composition.

6. A tooth restoration having a post and a crown, the improvement comprising said post being translucent and further being fired to said crown.

7. In a tooth restoration according to claim 6, the improvement further comprising said translucent post having a translucent core adjacent thereto.

8. In the tooth restoration according to claim 7, the improvement further comprising said translucent post and said translucent core consisting of a translucent ceramic material.

9. In the tooth restoration according to claim 8, the improvement further comprising said ceramic material being selected from the group consisting of glass-ceramics containing tetrasilicic mica and glass-ceramics containing tetrasilic fluormica.

10. In the tooth restoration according to claim 7, the improvement further comprising said translucent post and said translucent core consisting of an apatite-containing dental construct composition.

11. Method of restoring an endodontically prepared tooth comprising the steps of:
    (a) taking a first impression of said prepared tooth;
    (b) fabricating a translucent post from said first impression;
    (c) attaching said translucent post within said prepared tooth;
    (d) taking a second impression of said prepared tooth with said translucent post attached therein;
    (e) fabricating a crown from said second impression; and
    (f) attaching said crown to said translucent post.

12. The method according to claim 11, wherein the step of fabricating a translucent post is accomplished by the use of a translucent ceramic material.

13. The method according to claim 12, wherein the step of fabricating a translucent post is accomplished by the use of a translucent glass-ceramic material selected from the group consisting of glass-ceramics containing tetrasilicic mica and glass-ceramics containing tetrasilicic fluormica.

14. The method according to claim 13, wherein an endodontically treated tooth is prepared by removing the endodontic filling material to two-thirds of the depth of the roots of said tooth to form a canal, blending the axial walls of a crown preparation of said tooth on a curve to the axial walls of said canal, and cementing said translucent post into said canal.

15. The method according to claim 14, wherein a dentin bonding agent is utilized in the step of cementing said translucent post into said canal.

16. The method according to claim 15, wherein a light/chemical cured resin cement is utilized in the step of cementing said translucent post into said canal.

17. The method according to claim 12, wherein the step of fabricating a translucent post is accomplished by the use of a castable phosphate-bound, apatite-containing dental construct composition.

18. A prefabricated post for restoring a tooth, comprising a dental construct having a length greater than its average diameter, said dental construct being translucent and including a cylindrical shaft.

19. The prefabricated post according to claim 18, wherein said dental construct includes a tapered shaft.

20. The prefabricated post according to claim 18, wherein said dental construct has an etched surface thereon.